United States Patent [19]

Kinter et al.

[11] Patent Number: 5,051,400

[45] Date of Patent: Sep. 24, 1991

[54] METHOD OF TREATING NAUSEA AND EMESIS RELATED TO MOTION SICKNESS WITH VASOPRESSIN ANTAGONISTS

[75] Inventors: Lewis B. Kinter, Havertown, Pa.; Randall L. Kohl, Houston, Tex.

[73] Assignee: SmithKline Beecham Corporation, Philadelphia, Pa.

[21] Appl. No.: 545,259

[22] Filed: Jun. 28, 1990

[51] Int. Cl.⁵ .................. A61K 37/34; C07K 7/16
[52] U.S. Cl. ............................ 514/11; 514/9; 514/16; 514/872
[58] Field of Search ............ 514/9, 11, 16, 872

[56] References Cited

U.S. PATENT DOCUMENTS

| | | | |
|---|---|---|---|
| 4,399,125 | 8/1963 | Manning et al. | 514/11 |
| 4,469,679 | 9/1984 | Huffman et al. | 514/11 |
| 4,543,349 | 9/1985 | Callahan et al. | 514/11 |
| 4,649,130 | 3/1987 | Manning et al. | 514/11 |
| 4,714,696 | 12/1987 | Manning et al. | 514/11 |
| 4,717,715 | 1/1988 | Ali | 514/11 |
| 4,724,229 | 2/1988 | Ali | 514/11 |
| 4,760,052 | 7/1988 | Callahan et al. | 514/11 |
| 4,772,586 | 9/1988 | Manning et al. | 514/11 |
| 4,876,243 | 10/1989 | Marshall et al. | 514/11 |

*Primary Examiner*—Lester L. Lee
*Attorney, Agent, or Firm*—Stuart R. Suter; Stephen Venetianer; Edward T. Lentz

[57] ABSTRACT

Vasopressin derivatives having $V_1$ antagonist activity which alleviate the symptoms of motion sickness. More specifically, the vasopressin $V_1$ antagonists of this invention are employed to prevent nausea and emesis associated with motion. The antagonists may also be employed for preventing nausea and emesis due to other etiologies.

10 Claims, No Drawings

METHOD OF TREATING NAUSEA AND EMESIS RELATED TO MOTION SICKNESS WITH VASOPRESSIN ANTAGONISTS

This invention relates to vasopressin derivatives having $V_1$ antagonist activity. More specifically, the vasopressin derivatives of this invention are employed for treatment of nausea and emesis due to motion sickness.

BACKGROUND

It is well known that plasma vasopressin concentrations are elevated following emesis. It has been reported that arginine vasopressin (AVP) is a mediator of chemotherapy-induced emesis. In motion sickness studies, a sharp rise in AVP has been reported and it has been suggested that stimulation of AVP release may be the first and most significant response to stressful motion stimuli. In motion sickness studies recently conducted on astronauts, it was observed that the astronauts experiencing motion sickness exhibited high circulating plasma vasopressin concentrations. Thus, an emetic stimulus may stimulate vasopressinergic pathways in the brain which may stimulate the emetic center and thus result in emesis.

The pressor and antidiuretic activities of vasopressin are mediated by separate receptor pathways identified as $V_1$ and $V_2$, respectively. A number of synthetic modifications of the vasopressin structures have been reported to give antagonistic activities. U.S. Pat. No. 4,399,125 discloses vasopressin antagonists of the antidiuretic activity of arginine vasopressin. These peptide structures are characterized in that the 1 position has a 1-$\beta$-mercapto-$\beta,\beta$-cyclopentamethylenepropionic-acid group (Pmp). Basic $v_1$- vasopressin antagonists are disclosed in U.S. Pat. No. 4,604,378 characterized in that the peptides have an acyclic unit at position 1, i.e., a 1-desamino-penicillamine group. None of the known art discloses the biological activities of the claimed compositions and methods of this invention.

In the description herein and in the claims, the nomenclatue common in the art of peptide and more specifically, vasopressin chemistry is used. When no configuration is noted, the amino acid unit is in the L, or naturally occurring, form. The thio members of the $\beta$-mercapto-propionic acid (1) and cysteine (6) units are added for clarity in certain structural formulas.

Exemplary of the peptide abbreviations used herein are the following: Gly, glycine; Tyr, tyrosine; Phe, phenylalamine; Arg, arginine; Ile, isoleucine; Asn, asparagine; Val, valine; Gln, glutamine; Pro, proline; Leu, leucine; Lys, lysine; Cys, cysteine; Mpr, $\beta$-mercaptopropionic acid; d Pen, $\beta$-mercapto-$\beta$-$\beta$-dimethylpropionic acid; Ala, alanine.

It is an object of this invention to provide antagonists of vasopressin-mediated emetic responses. It is a further object to provide a method for preventing nausea and emesis due to motion sickness and other etiologies.

Examples of $V_1$ antagonists that may be employed in this invention are the des-Pro-vasopressin-like compounds set forth in U.S. Pat. No. 4,599,324, preferably [1-deaminopenicillamine-2-D-(o-ethyl)tyrosine-7-desproline-8-arginine 9-desglycine] vasopressin. Further examples of $V_1$-vasopressin antagonists useful in this invention are set forth in U.S. Pat. No. 4,604,378, U.S. Pat. No. 4,684,622, U.S. Pat. No. 4,658,015, and U.S. Pat. No. 4,684,624.

DESCRIPTION OF INVENTION

The vasopressin antagonists which are the active ingredients of the pharmaceutical compositions and employed in the methods of this invention are preferably represented by the following formula:

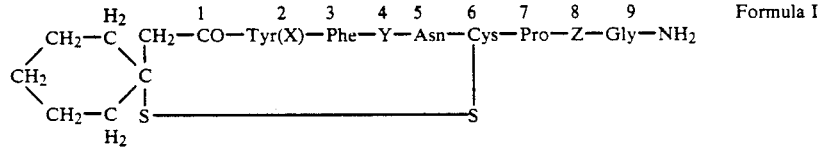

Formula I wherein X is H, methyl or ethyl, Y is Gln or Val and Z is L-or D-arg.

A particularly preferred compound in the pharmaceutical compositions and methods of this invention is a compound of Formula 1 in which X is methyl, Y is Gln and Z is L-arg being the compound [1-$\beta$-Mercapto-$\beta$-$\beta$-Cyclopentamethylenepropionic acid, 2-(0-methyl)tyrosine-8-arginine] vasopressin.

Also included in this invention are various derivatives of the compounds of Formula 1 such as addition salts, prodrugs in ester or amide forms and complexes, especially the nontoxic pharmaceutically acceptable salts. The acid addition salts are prepared in a standard manner in a suitable solvent from the parent compound and an excess of an acid, such as hydrochloric, hydrobromic, sulfonic, phosphine, acetic, maleic, succinic, ethanesulfonic or methanesulfonic acids.

The above compounds of Formula 1 which are the active ingredients in the compositions and method for treating nausea and emesis are prepared by synthetic methods well known to the art. For example, the compounds may be prepared by cyclizing a linear peptide intermediate of this invention by means of two mercapto groups located respectively in the cysteine unit at position 6 and in the $\beta$-mercaptopropionic acid unit at position 1. The cyclization reaction occurs in the presence of a mild oxidizing agent which, at high dilution, is capable of oxidizing intramolecularly the dimercaptan to a disulfide. U.S. Pat. Nos. 4,367,225 and 4,469,679 disclose the preparation and vasopressin activity of the compounds of Formula 1 and similar octapeptide vasopressin antagonists.

The activity of the compounds of Formula 1 was demonstrated in vivo with squirrel monkeys. The monkeys were tested using an apparatus which induces motion sickness symtomatology by combining vertical and rotational movements in a visually unrestricted laboratory environment. The stressor test lasted up to 60 minutes The animals were placed in 7×7×12 inch high clear plexiglas boxes which were rotated about the vertical axis at 25 rpm using a Contraves unit. The plexiglas housings were simultaneously sinusoidally oscillated at 0.5 HZ through a vertical distance of 6 inches. The rating scale used was similar to that developed by Graybiel et al., Aerospace Med. 39:453–5,1968, which allowed a maximum symptom score of 31 points. The rating scale used was as follows:

| MOTION SICKNESS RATING SCALE | |
| --- | --- |
| | Points |
| Minimal Qualifying Symptoms: | |
| Decreased activity and inquisitiveness | 1 |
| or | |
| Unusual posture | |
| Minimum Sickness: | |
| Decreased activity and alertness* | 2 |
| or | |
| Licking of lips | |
| Minor Sickness: | |
| Salivation (with or without foaming) | 4 |
| or | |
| Occasional chewing | |
| Major Sickness: | |
| Frequent, vigorous chewing | 8 |
| Vomiting or Retching | 16 |
| Maximum possible symptom points: | |
| *eyes frequently closed (sleepiness) | 31 |

The test was given pre-drug during the course of the 2 years prior to receiving the vasopressin antagonist on five separate trials. The on-drug trial was given 30 minutes after i.v. injection of the antagonist via the tail vein. The test was repeated approximately two weeks later without drug. All the monkeys were familiar with the experimental apparatus and demonstrated stable responses to tests over the previous two years.

The following table sets forth the results obtained when 200-240 mcg. of SKF 100273 $d(CH_2)_5$ Tyr (Me) AVP, was injected via the tail vein. This compound is a known vasopressin ($V_1$) antagonist.

TABLE I

| Monkey | Motion Sickness Rating[1] | | | Latency to Emesis (min.) | | |
| --- | --- | --- | --- | --- | --- | --- |
| | Predrug[2] | On-Drug[3] | Post Drug[4] | Predrug | On-Drug | Post Drug |
| 1 | 22.8 | 3 | 17 | 36.3 | 60+ | 40.0 |
| 2 | 20.6 | 2 | 18 | 32.2 | 60+ | 50.2 |
| 3 | 21.4 | 4 | 24 | 38.3 | 60+ | 45.5 |
| 4 | 21.6 | 5 | 22 | 26.4 | 60+ | 38.5 |
| Mean | 21.6 | 3.5 | 20.2 | 33.3 | 60[5] | 43.6 |
| SEM | 0.4 | 0.6 | 1.6 | 2.6 | — | 2.7 |

[1] Maximum symptom score is 31
[2] Motion sickness rating on tests given up to 2 years prior to drug test, 5 repititions
[3] 200-240 mcg d(CH$_2$)$_5$Tyr(Me)AVP, I.V., into each squirrel monkey (approx. 800-1000 g weight) 30 minutes prior to stressor test
[4] Test repeated approximately 2 weeks later without drug
[5] Testing was terminated after 60 minutes.

The test terminated at 60 minutes and it will be noted that without treatment monkeys vomited with a latency of 33.3±2.6 minutes and had 21.6±0.4 symptom points. Sixty minutes after receiving the compound no emesis was observed i.e. latency >60 minutes and symptom points did not exceed 3.5±0.6. When the animals were re-tested approximately two weeks later, symptomatology was 20.2±1.6 and latency to emesis was 43.6±2.7 minutes, returning to approximately predrug levels with all the monkeys reaching emesis.

These results clearly indicate that the $V_1$-vasopressin antagonist SKF 100273 dramatically prevents emesis and motion sickness symptomatology in squirrel monkeys.

The pharmaceutical compositions used to carry out the method of preventing emesis and motion sickness symptomatology in patients comprise a pharmaceutical carrier and, as the active ingredient, a vasopressin antagonist compound as defined above. The active ingredient will be present in the compositions in a nontoxic but effective amount to produce the anti-emetic activity and prevent symptoms of motion sickness.

Preferably, the compositions will contain the active ingredient of Formula 1 in an amount of from about 1.0 mg. to above 100 mg., advantageously from about 10 mg. to about 50 mg. per dosage unit.

The pharmaceutical carrier may be for example a solid or liquid. Preferably a liquid carrier is employed. Exemplary of liquid carriers are isotonic saline solutions, water, alcohols, polyethylene glycols and vegetable oils. Exemplary of solid carriers are lactose, gelatin, magnesium stearate stearic acid, pectin or acacia. The pharmaceutical compositions may also include additional agents such as buffers, salts for regulating osmotic pressure, emulsifiers and wetting agents.

A wide variety of pharmaceutical forms can be employed for example, the composition may take the form of aerosol nasal sprays, implants, sublingual tablets, dermal patches, emulsions, suppositories and gels.

Most advantageously the pharmaceutical forms for the compositions of this invention will be present as ampoules or multidose vials which are suitable for parenteral injection, for example, intravenous, subcutaneous or intramuscular administration.

The pharmaceutical compositions are prepared by conventional techniques involving procedures such as mixing, granulating and compressing or dissolving the ingredients as appropriate to the desired preparation.

The method of preventing emesis and symptoms of motion sickness according to this invention comprises administering to a subject in an amount sufficient to prevent these symptoms a vasopressin antagonist compound of Formula 1. Preferably the Compounds of Formula 1 are administered in conventional dosage unit forms prepared by combining an appropriate dose of the compound with standard pharmaceutical carriers.

The active ingredient will be administered in a daily dosage regimen from about 1.0 mg. to about 400 mg., preferably from about 10 mg. to about 200 mg. Advantageously, equal doses will be administered two to four times per day or by continuous intravenous infusion. When the administration is carried out as described above, an anti-emetic activity and prevention of symptoms associated with motion sickness is accomplished.

The route of administration of the pharmaceutical compositions and in accordance with the method of this invention is internal, preferably parenterally or by insufflation, in an amount to produce the desired biological activity.

The following examples are not limiting, but are merely illustrative of the compositions and method of this invention.

PARENTERAL DOSAGE UNIT COMPOSITIONS:

A preparation which contains 0.5 mg of the cyclic peptide of Formula 1 as a sterile dry powder for parenteral injection is prepared as follows: 0.5 mg of peptide amide is dissolved in 1 ml of an aqueous solution of 20 mg of mannitol. The solution is filtered under sterile conditions into a 2 ml ampoule and lyophylized. The powder is reconstituted before either intramuscular or intravenous injection to a subject suffering from emesis mediated by vasopressin. The injection is repeated as necessary, from 1–4 times daily or in continuous i.v. drug injection. Other vasopressin antagonists of this invention are made up and used in like manner.

NASAL DOSAGE UNIT COMPOSITIONS:

30 mg of finely ground $V_1$ antagonist of this invention such as disclosed in Formula 1 is suspended in a mixture of 75 mg of benzl alcohol and 1.395 g of a suspending agent such as a commercial mixture of semi-synthetic glycerides of higher fatty acids. The suspension is placed in an aerosol 10 ml container which is closed with a metering valve and charged with aerosol propellants. The contents comprise 100 unit doses which are administered intranasally to a subject from 1–4 times a day.

What is claimed:

1. A method for antagonizing vasopressin mediated emetic responses in a subject in need thereof which comprises administering to said subject an effective, nontoxic quantity of a $V_1$ vasopressin antagonist together with a pharmaceutically acceptable carrier.

2. The method of claim 1 which comprises administering the antagonist parenterally or intranasally.

3. The method of claim 2 in which the $V_1$ antagonist is [1-β-mercapto-β,β-cyclopentamethylenepropionic acid, 2-(0-methyl) tyrosine-8-arginine] vasopressin.

4. A method of producing anti-emetic activity in a subject in need thereof which comprises administering to said subject an effective, nontoxic quantity of a $V_1$-vasopressin antagonist having the formula:

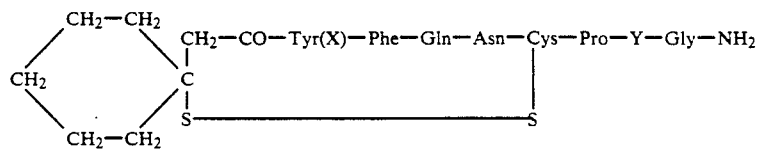

wherein X is hydrogen, methyl or ethyl and Y is L-or D-Arg or a pharmaceutically acceptable salt thereof together with a pharmaceutical acceptable carrier.

5. The method of claim 4 in which X is methyl and Y is L-Arg. being the compound [1-β-mercapto-β,β-cyclopentamethylenepropionic acid, 2-(0-methyl) tyrosine-8-arginine] vasopressin.

6. The method of claim 4 which comprises administering a dosage unit containing from about 1.0 mg. to about 100 mg. of the $V_1$ antagonist.

7. The method of claim 4 which comprises administering the antagonist parenterally or intranasally.

8. A method for inhibiting motion associated emesis in a subject in need thereof which comprises administering to said subject an effective, nontoxic quantity of the $V_1$ antagonist of claim 4.

9. The method of claim 8 in which the $V_1$ antagonist is [1-β-mercapto-β,β-cyclopentamethylenepropionic acid, 2-(0-methyl) tyrosine-8-arginine] vasopressin.

10. The method of alleviating symptoms associated with motion sickness in a subject in need thereof which comprises administering to said subject an effective, nontoxic quantity of the antagonist of claim 4.

* * * * *